(12) United States Patent
Koch et al.

(10) Patent No.: US 7,083,831 B1
(45) Date of Patent: Aug. 1, 2006

(54) CHROMIUM-FREE CORROSION PREVENTIVE AND CORROSION PREVENTION METHOD

(75) Inventors: Matthias Koch, Duesseldorf (DE); Kerstin Motzkat, Oberhausen (DE); Karsten Hackbarth, Duesseldorf (DE); Joerg Sander, Velbert (DE)

(73) Assignee: Henkel Kommanditgesellschaft Auf Aktien (Henkel KGAA), Duesseldorf (DE)

( * ) Notice: Subject to any disclaimer, the term of this patent is extended or adjusted under 35 U.S.C. 154(b) by 0 days.

(21) Appl. No.: 09/979,286

(22) PCT Filed: May 10, 2000

(86) PCT No.: PCT/EP00/04151

§ 371 (c)(1),
(2), (4) Date: Nov. 19, 2001

(87) PCT Pub. No.: WO00/69978

PCT Pub. Date: Nov. 23, 2000

(30) Foreign Application Priority Data

May 19, 1999 (DE) .............................. 199 23 118

(51) Int. Cl.
*C08F 2/46* (2006.01)
(52) U.S. Cl. .................. 427/515; 526/279; 526/241; 427/508; 427/503; 427/496; 427/487
(58) Field of Classification Search ................ 427/503, 427/508, 515, 496, 487; 526/279, 241
See application file for complete search history.

(56) References Cited

U.S. PATENT DOCUMENTS

| | | | | |
|---|---|---|---|---|
| 3,719,541 A | * | 3/1973 | Takahashi et al. ....... | 156/275.5 |
| 4,548,963 A | * | 10/1985 | Cluff et al. ................. | 523/427 |
| 4,748,087 A | * | 5/1988 | Davidson et al. ........... | 428/463 |
| 5,344,504 A | | 9/1994 | Deck et al. ................ | 148/243 |
| 5,580,614 A | * | 12/1996 | Amberg-Schwab et al. | 427/493 |

FOREIGN PATENT DOCUMENTS

| | | |
|---|---|---|
| DE | 37 28 720 | 3/1989 |
| DE | 41 22 743 | 11/1992 |
| DE | 197 51 153 | 5/1999 |
| DE | 197 54 108 | 6/1999 |
| EP | 0 685 534 | 12/1995 |
| EP | 0 694 593 | 1/1996 |
| EP | 0 792 922 | 9/1997 |
| FR | 2 752 577 | 2/1998 |
| WO | WO95/04169 | 2/1995 |
| WO | WO 95/14117 | 5/1995 |
| WO | WO 98/47631 | 10/1998 |

* cited by examiner

*Primary Examiner*—Margaret G. Moore
(74) *Attorney, Agent, or Firm*—Woodcock Washburn LLP

(57) ABSTRACT

A chromium-free corrosion inhibitor containing at least one titanium, silicon and/or zirconium compound corresponding to general formula (I):

$$[\underset{R^2}{\underset{|}{C}}=\underset{R^1}{\overset{|}{C}}-\underset{R^3}{\overset{|}{C}}-\overset{O}{\overset{\|}{C}}-O]_n-Me-O-X_{4-n} \quad (I)$$

in which Me is a titanium, silicon or zirconium ion, at least one other olefinically unsaturated comonomer containing at least two olefinically unsaturated double bonds per molecule, optionally other comonomers containing one olefinically unsaturated double bond per molecule, and at least one radical and/or cationic polymerization initiator that is activated by radiation.

10 Claims, No Drawings

CHROMIUM-FREE CORROSION PREVENTIVE AND CORROSION PREVENTION METHOD

CROSS-REFERENCE TO RELATED APPLICATIONS

This application is a U.S. National Stage application filed under 35 U.S.C. § 371 of International Application No. PCT/EP00/04151, filed May 10, 2000, in the European Patent Office, claiming priority under 35 U.S.C. §§ 119 and 365 of PCT/EP00/04151 and DE 199 23 118.4, filed on May 19, 1999, in the German Patent Office.

This invention relates to a chromium-free organic/organometallic corrosion inhibitor and to a corrosion-inhibiting process for the treatment of surfaces of steel—optionally provided with a metallic coating of zinc, aluminium, copper, nickel, etc.—or of aluminium and its alloys. It is particularly suitable for surface treatment in coil coating plants for the use of these substrates in the domestic and architectural sectors and in the automotive industry.

For temporary protection against corrosion, galvanized or alloy-galvanized steel strip is either simply coated with corrosion-inhibiting oils or—where there is a more serious risk of corrosion—is phosphated or chromated. The final coating step using organic binders (primers, paints) is generally preceded by a multistage process. For the use of galvanized metal strip or aluminium and its alloys in the domestic appliance and architectural industries, the metal surface is first provided with a corrosion-inhibiting layer, optionally after removal of the oil layer. The best known anti-corrosion measure is chromating where the metal surface is coated with a chromium(III) and/or chromium(VI)-containing layer generally containing about 5 to 15 mg/m$^2$ chromium. Phosphating as an alternative temporary anti-corrosion measure has two disadvantages: first, the appearance of the metal surfaces can be undesirably altered and, second, phosphating is equipment-intensive because—depending on the substrate material—it involves an additional activation step and generally a post-phosphating passivation step. Besides the actual protection against corrosion, the inorganic coating ensures good adhesion to the primer applied thereto. The primer in turn not only favorably influences the corrosion-inhibiting effect of the inorganic conversion layer, it also provides the finishing paint with a good adhesion base.

Metal plates are also being increasingly supplied by the finisher with a base coat which, for example, facilitates such machining operations as stamping, drilling, grooving, profiling and/or deep drawing. Besides corrosion-inhibiting properties, this base coat is also expected to make the plate easier to machine. Another function of such base coats is to establish an adhesion base for following aesthetic surface coatings. A workpiece made from correspondingly pretreated plate material by machining may then be coated with a finishing paint in a concluding step. The base coat according to the invention also preferably serves as a primer, in which case surface coating is carried out immediately afterwards in the coil coater. In this case, only the fully coated plate material is subjected to further processing. It is known that coil coating consists essentially of three steps. In the first step, the metal strip is cleaned and provided with an (inorganic) pretreatment layer; in the second step, the primer is applied and, in the concluding third step, the finishing paint is applied. In some applications, varnish or protective film coatings may also be applied. Attempts have already been made to use the pretreatment step for the functions performed by the base coat described above. To this end, a suitable organic polymer capable of forming a surface film with the functional properties demanded of a base coat is added, for example, in the inorganic conversion treatment.

U.S. Pat. No. 5,344,504, for example, describes a process for coating galvanized steel in which the substrate is coated with a treatment solution having the following composition: 0.1 to 10 g/l of a tetra- or hexafluoro acid of boron, silicon, titanium and zirconium or hydrofluoric acid, ca. 0.015 to ca. 6 g/l cations of cobalt, copper, iron, manganese, nickel, strontium or zinc and optionally up to about 3 g/l of a polymer selected from polyacrylic acid, polymethacrylic acid and esters thereof. The pH value of this treatment solution is in the range from about 4 to about 5.

WO 95/14117 also describes a process for treating surfaces of zinc or aluminium or alloys thereof. In this process, the surfaces are contacted with a treatment solution having a pH below 3 which contains a complex between a metal oxo-ion and a hetero-ion. The metal oxo-ion is selected from molybdate, tungstate and vanadate. The hetero-ion is selected from phosphorus, aluminium, silicon, manganese, magnesium, zirconium, titanium, tin, cerium and nickel. The treatment solution also contains an inorganic film former which is compatible with the other components of the solution. Suitable film formers are, for example, polyacrylates such as, in particular, polymers of methyl methacrylate, n-butyl acrylate, hydroxyethyl acrylate and glycerol propoxytriacrylate.

EP-A-694 593 recommends treating the metal surfaces with a treatment solution containing the following components: an organic polymer or copolymer where 0.5 to 8% of the monomers bear groups capable of forming compounds with metal ions, complex cations or anions of aluminium, calcium, cerium, cobalt, molybdenum, silicon, vanadium, zirconium, titanium, trivalent chromium and zinc, an oxidizing agent, such as nitric acid, perchloric acid or hydrogen peroxide, and an acid such as, for example, oxalic acid, acetic acid, boric acid, phosphoric acid, sulfuric acid, nitric acid or hydrochloric acid.

WO 95/04169 teaches the treatment of metal surfaces with a treatment solution containing at least one of the following components: fluorocomplexes of titanium, zirconium, hafnium, silicon, aluminium and boron, metal ions selected from cobalt, magnesium, manganese, zinc, nickel, tin, copper, zirconium, iron and strontium, phosphates or phosphonates and water-soluble or water-dispersible organic film formers.

EP-A-792 922 describes a chromium-free corrosion-inhibiting coating composition for aluminium or aluminium alloys which contains a film-forming organic polymer and (i) a salt selected from esters of rare earth metals, alkali metal or alkaline earth metal vanadate and (ii) a borate salt of an alkaline earth metal. Preferred polymers mentioned include, for example, epoxides, including polyimide-based epoxides, polyurethanes, acrylic polymers and alkyd-based systems. Accordingly, this coating composition must contain at least one borate and one other component which may be a vanadate in addition to the organic film former.

EP-A-685 534 describes a process for protecting a steel substrate by a thin film of an organic/inorganic hybrid polymer based on an alkoxysilane, another condensible organometallic compound with the formula M(OR)$_4$ and (meth)acrylic acid, water and a polymerization initiator. The coating is formed by thermal or photopolymerization. Zirconium and titanium are mentioned as metals for the organometallic compound. It is stated that the film in question protects steel substrates against corrosion and oxidation. In addition, the coating is said to protect the substrate against shock and other mechanical effects.

WO 98/47631 describes a process for the remedial treatment of defectively pretreated metal surfaces. To this end, the defective metal surfaces are coated with an aqueous acidic solution containing fluorometallate anions, divalent or trivalent cations of cobalt, magnesium, manganese, zinc, nickel, tin, copper, zirconium, iron and strontium; phosphorus-containing inorganic oxo anions and phosphonate anions and a water-soluble and/or water-dispersible organic polymer and/or a polymer-forming resin. The document in question does not indicate whether the compositions in question are also suitable for the first-time treatment of non-precoated metal strip.

Hitherto unpublished DE-A-197 54 108.9 describes a chromium-free water-based corrosion inhibitor for the treatment of surfaces of galvanized or alloy-galvanized steel and of aluminium. It contains as key components hexafluoro anions of titanium and/or zirconium, vanadium ions, cobalt ions, phosphoric acid and preferably an organic, more particularly polyacrylate-based, film former. This corrosion inhibitor is particularly suitable for the anti-corrosion treatment of metal strip.

Hitherto unpublished DE 197 51 153.8 describes polymerizable chromium-free organic compositions containing titanium, manganese and/or zirconium salts of olefinically unsaturated polymerizable carboxylic acids and other olefinically unsaturated comonomers and a radical polymerization initiator and their use for the organic coil coating of metallic materials. Although these nonaqueous polymerizable compositions allow the chromium-free pretreatment of steels with corrosion-inhibiting properties, these corrosion-inhibiting properties are in need of improvement for many applications.

Despite the extensive prior art, there is still a need for improved corrosion inhibitors and coating processes for metal surfaces which would provide for the chromium-free pretreatment of the metal substrates and for effective corrosion prevention without the use of acids or high fluoride levels. The constituents would preferably be homogeneously dissolved or dispersed in the composition to avoid separation during production. transportation, storage and use.

The coating would facilitate the stamping and forming of the workpieces from the coated metal strip. In addition, the layers of the metal substrates would withstand the other fabrication steps up to assembly of the products such as, for example, cleaning, optionally phosphating, riveting, welding and would lend themselves to coating with a finishing paint either directly or after machining. In the interests of pollution control and works safety, the treatment process would be able to be carried out without the use of chromium compounds and in the absence of organic solvents. The principal fields of application would be the domestic appliance and architectural industries mentioned above.

DESCRIPTION OF THE INVENTION

The solution to the problem as provided by the present invention is defined in the claims and consists essentially in the provision of a chromium-free corrosion inhibitor containing:

at least one titanium, silicon and/or zirconium compound corresponding to general formula (I):

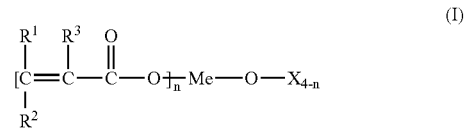

in which $R^1$ and/or $R^2$ represent H, $C_{1-12}$ alkyl, aralkyl or the group —CO—O—Y, $R^3$ is H or $C_{1-12}$ alkyl, Me is a titanium, silicon or zirconium ion, X is H, $C_{1-12}$ alkyl, aryl or aralkyl, alkoxyl, aroxyl, sulfonyl, phosphate, pyrophosphate, Y is H, $C_{1-12}$ alkyl or Me and n=0 to 4, at least one other olefinically unsaturated comonomer containing at least two olefinically unsaturated double bonds per molecule, optionally other comonomers containing one olefinically unsaturated double bond per molecule, at least one radical and/or cationic polymerization initiator.

In a preferred embodiment, the corrosion inhibitor contains no additional solvent. All the ingredients of the corrosion inhibitor should react off completely in the course of the process described hereinafter and should remain in the coating to be produced.

The present invention also relates to a process for the corrosion-inhibiting treatment of steel—optionally provided with a metallic coating of zinc, aluminium, copper, nickel or similar metals—or aluminium or its alloys which comprises the following key process steps:

a) contacting the surface of the substrate with a corrosion inhibitor of the above-mentioned type for 0.5 to 60 seconds at a treatment temperature of 10 to 50° C. and preferably in the range from 15 to 35° C., b) removing the excess corrosion inhibitor, if any, from the surface and c) crosslinking the polymeric film and anchoring it on the metal surface by suitable supply of energy for 0.1 to 120 seconds.

In a preferred embodiment, the corrosion inhibitor is applied to the surface of the workpiece, preferably metal strip, by flooding/squeezing, spraying/squeezing, film application (for example by the curtain flow process), suitable stripper or roller applications.

Specific examples of the titanium, silicon and/or zirconium compounds of formula (I) to be used in accordance with the invention are isopropyl dimethacrylisostearoyl titanate, isopropyl tri(dodecyl)-benzenesulfonyl titanate, isopropyl tri(octyl)phosphatotitanate, isopropyl (4-amino) benzenesulfonyl-di-(dodecyl)benzenesulfonyl titanate, alkoxyl trimethacryltitanate, isopropyl tri(dioctyl)pyrophosphatotitanate, alkoxy triacryltitanate, isopropyl tri(N-ethylenediamino)ethyl titanate, di(cumyl)phenyl oxoethylene titanate, di(dioctyl)pyrophosphate oxoethylene titanate, dimethyl oxoethylene titanate, di(butylmethyl)pyrophosphate oxoethylene di(dioctyl)phosphitotitanate, di(dioctyl) phosphatoethylene titanate, di(butylmethyl)pyrophosphatoethylene titanate, tetraethyl titanate, tetraisopropyl titanate, tetra-n-propyl titanate, tetra-n-butyl titanate, n-butyl polytitanate, tetra-2-ethylhexyl titanate, tetraisooctyl titanate, isostearoyl titanate, monomeric cresyl titanate, polymeric cresyl titanate, octyleneglycol titanate, titanyl acetyl acetonate, diisopropoxy-bis-ethyl acetoacetatotitanate, di-n-butoxy-bis-ethyl acetoacetatotitanate, diisobutoxy-bis-ethyl acetoacetatotitanate, triethanolamine titanate, isopropyl triisostearoyl titanate, adducts of 2-(N,N-dimethylamino) isobutanol, triethyl amine, (meth)acrylate-functionalized amine derivative, methacrylamide-functionalized amine derivative with di(dioctyl)phosphatoethylenetitanate, tetraisopropyl di(dioctyl)phosphititotitanate, tetraoctyl di(ditridecyl)phosphititotitanate, tetra-(2,2-diallyloxymethyl)butyl di(ditridecyl)phosphititotitanate, neopentyl (diallyl)oxytrineodecanoyl titanate, neopentyl (diallyl)oxytri(dodecyl)benzenesulfonyl titanate, neopentyl (diallyl)oxytri(dioctyl)phosphatotitanate, neopentyl (diallyl)oxytri(dioctyl) pyrophosphatotitanate, neopentyl (diallyl)oxytri(N-ethylenediamino)ethyl titanate, neopentyl (diallyl)oxytri(m-amino)phenyl titanate, neopentyl (diallyl) oxytrihydroxycaproyl titanate, cyclo(dioctyl) pyrophosphatodioctyl titanate, dicyclo(dioctyl) pyrophosphatodioctyl titanate, 2-(acryloxyethoxy)-trimethyl silane, N-(3-acryloxy-2-hydroxypropyl)-3-aminopropyl triethoxysilane, (3-acryloxypropyl)dimethylmethoxysilane, (3-acryloxypropyl)methylbis(trimethylsiloxy)silane, (3-acryloxypropyl)methyl dimethoxysilane, (3-acryloxypropyl) trimethoxysilane, (3-acryloxypropyl)tris(trimethylsiloxy)-silane, acryloxytrimethylsilane, 1,3-bis((acryloxymethyl) phenethyl)-tetramethyl disiloxane, bis(methacryloxy) diphenylsilane, 1,3-bis(3-methacryloxypropyl)tetrakis (trimethylsiloxy)disiloxane, 1,3-bis(3-methacryloxypropyl) tetramethyldisiloxane, 1,3-bis(methacryloxy)-2-trimethylsiloxypropane, methacrylamidopropyl triethoxysilane, methacrylamidotrimethylsilane, methacryloxyethoxytrimethylsilane, N-(3-methacryloxy-2-hydroxypropyl)-3-aminopropyl triethoxysilane, (methacryloxymethyl)bis(trimethylsiloxy)methylsilane, (methacryloxymethyl)dimethylethoxysilane, (methacryloxymethyl)phenyldimethylsilane, methacryloxymethyltriethoxysilane, methacryloxymethyltrimethoxysilane, methacryloxymethyltrimethylsilane, methacryloxymethyltris (trimethylsiloxy)silane, O-methacryloxy(polyethyleneoxy) trimethylsilane, 3-methacryloxypropyl bis(trimethylsiloxy) methylsilane, 3-methacryloxypropyl dimethylethoxysilane, methacryloxypropyl dimethylmethoxysilane, methacryloxypropyl methyl diethoxysilane, methacryloxypropyl methyl dimethoxysilane, methacryloxypropyl pentamethyldisiloxane, methacryloxypropylsilatrane, methacryloxypropyl triethoxysilane, methacryloxypropyl trimethoxysilane, methacryloxypropyl tris(methoxyethoxy)silane, methacryloxypropyl tris(trimethylsiloxy)silane, methacryloxypropyl tris(trimethylsiloxy)silane, methacryloxypropyl tris(vinyldimethylsiloxy)silane, methacryloxy trimethylsilane, tetrakis(2-methacryloxyethoxy)silane, Zr-hexafluoropentanedionate, Zr-isopropoxide, Zr-methacryloylethyl acetoacetate tri-n-propoxide, Zr-2-methyl-2-butoxide, Zr-2,4-pentanedionate, Zr-n-propoxide, Zr-2,2,6,6-tetramethyl-3,5-heptanedionate, Zr-trifluoropentanedionate, Zr-trimethylsiloxide, dicyclopentadienyl zirconium diethoxide, Zr-2-ethyl hexanoate, Zr-methacrylate, Zr-dimethacrylate.

Suitable comonomers containing at least two olefinically unsaturated double bonds per molecule are any of a number of comonomers, for example esterification products of alkane polyols, polyester polyols, polyether polyols or polyepoxides optionally containing hydroxyl groups with olefinically unsaturated carboxylic acids such as, for example, acrylic acid, methacrylic acid, itaconic acid, crotonic acid, maleic acid, maleic acid semiester, fumaric acid, fumaric acid semiester or reactive carboxyfunctional macromonomers or mixtures thereof. Other suitable comonomers containing at least two reactive double bonds per molecule are (meth)acrylate-functional polysiloxanes, (meth)acrylate-functional aliphatic, cycloaliphatic and/or aromatic polyepoxides and polyurethane compounds containing reactive (meth)acrylate groups. The above-mentioned comonomers containing at least two olefinically unsaturated double bonds per molecule typically have molecular weights in the range from 600 to 50,000 and preferably in the range from 1,000 to 10,000.

Specific examples of alkane polyols are butane-1,4-diol, hexane-1,6-diol, octane-1,8-diol and higher homologs thereof, glycerol, trimethylol propane, pentaerythritol and alkoxylation products thereof.

Besides the above-mentioned alkane polyols, suitable polyols are liquid polyhydroxy compounds containing two or three hydroxyl groups per molecule such as, for example, di- and/or trifunctional polypropylene glycols with molecular weights in the range from 200 to 6,000 and preferably in the range from 400 to 3,000. Statistical and/or block copolymers of ethylene oxide and propylene oxide may also be used. Another group of preferred polyethers are the polytetramethylene glycols which may be produced, for example, by the acidic polymerization of tetrahydrofuran. The molecular weights of the polytetramethylene glycols are in the range from 200 to 6,000 and preferably in the range from 400 to 4,000.

Other suitable polyols are the liquid polyesters obtainable by condensation of di- or tricarboxylic acids such as, for example, adipic acid, sebacic acid, glutaric acid, azelaic acid, suberic acid, 3,3-dimethylglutaric acid, terephthalic acid, isophthalic acid, hexahydrophthalic acid or dimer fatty acid with low molecular weight diols or triols such as, for example, ethylene glycol, propylene glycol, diethylene glycol, triethylene glycol, dipropylene glycol, butane-1,4-diol, hexane-1,6-diol, decane-1,10-diol, dimer fatty alcohol, glycerol or trimethylolpropane. Another group of polyol components suitable for use in accordance with the invention are the polyesters based on ε-caprolactone which are also known as polycaprolactones. However, polyesterpolyols of oleochemical origin may also be used. Polyester polyols such as these may be produced, for example, by complete ring opening of epoxidized triglycerides of a fatty mixture—containing at least partly olefinically unsaturated fatty acids—with one or more alcohols containing 1 to 12 carbon atoms and subsequent partial transesterification of the triglyceride derivatives to form alkyl ester polyols containing 1 to 12 carbon atoms in the alkyl moiety. Other suitable polyols are polycarbonate polyols and dimer diols (Henkel) and castor oil and its derivatives. The hydroxyfunctional polybutadienes commercially obtainable, for example, as "Poly-bd" may also be used as polyols for the compositions according to the invention.

Also suitable for the purposes of the present invention are one or more radical-polymerizable polyurethane compounds (A), (B) and/or (C) corresponding to general formula (II):

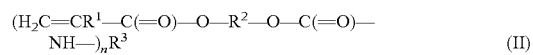

(II)

in which $R^1$ is hydrogen or a methyl group, $R^2$ is a linear or branched alkyl group containing 2 to 6 carbon atoms or alkylene oxides containing 4 to 21 carbon atoms and n is the number 1, 2 or 3, (A) where n is 1, $R^3$ is an aryl group containing 6 to 18 carbon atoms, a linear or branched alkyl group containing 1 to 18 carbon atoms or a cycloalkyl group containing 3 to 12 carbon atoms;

(B) where n=2, $R^3$ is

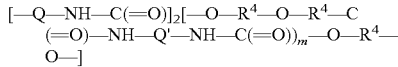

in which m=0 to 10 and $R^4$ is a) a polycaprolactone diol residue, b) a polytetrahydrofurfuryl diol residue or c) a diol residue which is derived from a polyester diol and has a molecular weight of 1,000 to 20,000, or (C) where n=3, $R^3$ is

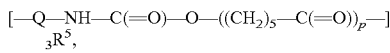

in which $R^5$ is a triol residue of a $C_{3-6}$ linear or branched trihydric alcohol and p is a number of 1 to 10 and Q and Q' independently of one another are $C_{6-18}$ aromatic, aliphatic or cycloaliphatic groups derived from diisocyanates or diisocyanate mixtures.

Examples of suitable aromatic polyisocyanates are any isomers of toluene diisocyanate (TDI) either in pure isomer form or in the form of a mixture of several isomers, naphthalene-1,5-diisocyanate, diphenyl methane-4,4'-diisocyanate (MDI), diphenylmethane-2,4'-diisocyanate and mixtures of 4,4'-diphenylmethane diisocyanate with the 2,4'-isomer or mixtures thereof with higher oligomers (so-called crude MDI), xylylene diisocyanate (XDI), 4,4'-diphenyldimethylmethane diisocyanate, di- and tetraalkyldiphenylmethane diisocyanate, 4,4'-dibenzyldiisocyanate, 1,3-phenylene diisocyanate, 1,4-phenylene diisocyanate. Examples of suitable cycloaliphatic polyisocyanates are the hydrogenation products of the above-mentioned aromatic diisocyanates such as, for example, 4,4'-dicyclohexylmethane diisocyanate ($H_{12}$MDI), 1-isocyanatomethyl-3-isocyanato-1,5,5-trimethyl cyclohexane (isophorone diisocyanate, IPDI), cyclohexane-1,4-diisocyanate, hydrogenated xylylene diisocyanate ($H_6$XDI), 1-methyl-2,4-diisocyanato-cyclohexane, m- or p-tetramethyl xylene diisocyanate (m-TMXDI, p-TMXDI) and dimer fatty acid diisocyanate. Examples of aliphatic polyisocyanates are tetramethoxybutan-1,4-diisocyanate, butane-1,4-diisocyanate, hexane-1,6-diisocyanate (HDI), 1,6-diisocyanato-2,2,4-trimethylhexane, 1,6-diisocyanato-2,4,4-trimethylhexane, butane-1,4-diisocyanate and 1,12-dodecane diisocyanate ($C_{12}$DI).

Suitable epoxy resin constituents for the olefinically unsaturated comonomers containing at least two olefinically unsaturated double bonds per molecule are any of a number of polyepoxy compounds containing at least two 1,2-epoxy groups per molecule. The epoxy equivalent of these polyepoxy compounds may vary between 150 and 4,000. Basically, the polyepoxy compounds may be saturated, unsaturated, cyclic or acyclic, aliphatic, alicyclic, aromatic or heterocyclic polyepoxy compounds. Examples of suitable polyepoxy compounds include the polyglycidyl ethers obtained by reaction of epichlorohydrin or epibromohydrin with a polyphenol in the presence of alkali. Polyphenols suitable for this purpose are, for example, resorcinol, pyrocatechol, hydroquinone, bisphenol A (bis(4-hydroxyphenyl)-2,2-propane), bisphenol F (bis-(4-hydroxyphenyl)-methane), bis-(4-hydroxyphenyl)-1,1-isobutane, 4,4'-dihydroxybenzophenone, bis-(4-hydroxyphenyl)-1,1-ethane, 1,5-hydroxynaphthalene. Other basically suitable polyepoxides are the polyglycidyl ethers of polyalcohols or diamines. These polglycidyl ethers are derived from polyalcohols, such as ethylene glycol, diethylene glycol, triethylene glycol, 1,2-propylene glycol, 1,4-butylene glycol, triethylene glycol, pentane-1,5-diol, hexane-1,6-diol or trimethylol propane. Other polyepoxides are polyglycidyl esters of polycarboxylic acids, for example reactions of glycidol or epichlorohydrin with aliphatic or aromatic polycarboxylic acids, such as oxalic acid, succinic acid, glutaric acid, terephthalic acid or dimer fatty acid. Other epoxy compounds are derived from the epoxidation products of olefinically unsaturated cycloaliphatic compounds.

Specific examples of di-, tri- or polyfunctional (meth)acrylates suitable for use in accordance with the invention are the following compounds: 1,3-butyleneglycol di(meth)acrylate, 1,4-butanediol di(meth)acrylate, 1,6-hexanediol di(meth)acrylate, bisphenol-A-epoxide di(meth)acrylate, alkoxylated bisphenol-A-di(meth)acrylate, polyalkyleneglykol di(meth)acrylate, trialkyleneglycol diacrylate, tetraalkyleneglycol di(meth)acrylate, neopentylglycol di(meth)acrylate, alkoxylated neopentylglykol di(meth)acrylate, trialkylolalkane tri(meth)acrylate, alkoxylated trialkylolalkane tri(meth)acrylate, glycerol alkoxytri(meth)acrylate, pentaerythritol tri(meth)acrylate, tris-(2-hydroxyalkyl)isocyanurate tri(meth)acrylate, acid-group-containing tri(meth)acrylate compounds, trimethylolpropane tri(meth)acrylate, trisalkoxy trimethylolpropane tri(meth)acrylate, ditrimethylolpropane tetra (meth)acrylate, pentaerythritol tetra(meth)acrylate, alkoxylated pentaerythritol tetra(meth)acrylate, dipentaerythritol penta(meth)acrylate, dipentaerythritol hexa(meth)acrylate, "alkylene" standing for ethylene, propylene or butylene and "alkoxy" for ethoxy, 1,2- or 1,3-propoxy or 1,4-butoxy.

The following (meth)acrylate monomers may also be used: amine-modified polyether acrylate oligomers, carboxyfunctionalized multifunctional (meth)acrylates, multifunctional melamine acrylates, difunctional silicone acrylates.

The following (meth)acrylates may be used as monofunctional comonomers: n-/iso-alkyl (meth)acrylate, cyclohexyl (meth)acrylate, 4-tert.-Butyl cyclohexyl (meth)acrylate, dihydrodicyclopentadienyl (meth)acrylate, tetrahydrofurfuryl (meth)acrylate, isobornyl (meth)acrylate (IBOA), β-carboxyethyl (meth)acrylate (β-CEA); mono(meth)acryloylalkyl phthalates, -succinate, -maleate; 2-(2-ethoxyethoxy)-ethyl (meth)acrylate, 2-phenoxyalkyl (meth)acrylate, alkanediol mono(meth)acrylate, allyl (meth)acrylate, hydroxyalkyl (meth)acrylate, 2,3-epoxyalkyl (meth)acrylate, N,N-dialkylaminoalkyl (meth)acrylate, N,N-dialkyl (meth)acrylamide, monoalkoxy trialkyleneglycol (meth)acrylat, monoalkoxy neopentylglycol alkyloxylate (meth)acrylate, polyalkylene glycol (meth)acrylate, alkoxylated nonylphenol (meth)acrylate, the alkyl groups containing 1 to 12 carbon atoms and "alkoxy" standing for ethoxy, 1,2- or 1,3-propoxy or 1,4-butoxy.

The compositions according to the invention are preferably cured by a UV or electron-beam curing process. This curing process may take place by radical or cationic polymerization according to the initiators and monomers used.

Suitable initiators for this radical or cationic polymerization are, for example, the following initiators: 1-hydroxycyclohexyl phenylketone, (η-5,2,4-cyclopentadien-1-yl)-[(1,2,3,4,5,6-η)-(1-methylethyl)benzene]iron(1+)- hexafluorophosphate(1−), 2-benzyldimethylamino-1-(4-morpholinophenyl)-1-butanone, benzildimethylketal dimethoxyphenyl acetophenone, bis(η5-2,4-cyclopentadien-1-yl)-bis[2,6-difluoro-3-(1H-pyrrol-1-yl)phenyl]-titanium, bis(2,4,6-trimethylbenzoyl)-phenylphosphine oxide (BAPO2), 2-methyl-1-[4-(methylthio)-phenyl]-2-morpholino-1-propanone, 1-(4-(1-methylethyl)-phenyl)-2-hydroxy-2-methyl-1-propan-1-one, 2-hydroxy-2-methyl-1-phenylpropan-1-one, 1,2-diphenylethane-1,2-dione, 1-[4-(2-hydroxyethoxy)-phenyl]-2-hydroxy-2-methyl-1-propan-1-one, (2,4,6-trimethylbenzoyl)-diphenylphosphine-oxide, α-hydroxybenzyl phenylketone, triarylsulfonium-hexafluoroantimonate salts, triarylsulfonium hexafluorophosphate salts, oligo-(2-hydroxy-2-methyl-1-[4-(1-methylvinyl)phenyl]propanone), 1-propanone, 2-hydroxy-2-methyl-1-[4-(1-methylethyl)phenyl]-homopolymer, phosphonic acid benzoyl-bis(2,6-dimethylphenyl)ester, benzophenone, methyl-ortho-benzoyl benzoate, methylbenzoylformate, 2,2-diethoxy acetophenone, 2,2-di-sec-butoxyacetophenone, [4-(4-methyl-phenylthio)phenyl]phenylmethanone-4-benzoyl-4'-methyldiphenylsulfide, p-phenylbenzophenone, 2-isopropylthioxanthone, 2-methyl anthraquinone, 2-ethyl anthraquinone, 2-chloroanthraquinone, 1,2-benzanthraquinone, 2-t-butylanthraquinone, 1,2-benzo-9,10-anthraquinone, benzil, benzoin, benzoin methylether, benzoin ethylether, benzoin isopropylether, α-methylbenzoin, α-phenylbenzoin, Michler's ketone, benzophenone, 4,4'-bis-(diethylamino)benzophenone, acetophenone, diethoxyphenyl acetophenone, thioxanthone, diethyl thioxanthone, 1,5-acetonaphthalene, ethyl-p-dimethyl aminobenzoate, benzilketones, 2,4,6-trimethylbenzoyl diphenyl phosphine oxides, benzilketal-(2,2-dimethoxy-1,2-diphenylethanone), 1-hydroxycyclohexyl phenylketone, 2-methyl-1[4-(methylthio)phenyl]-2-morpholino-1-propanone and/or 2-hydroxy-2-methyl-1-phenyl-1-propane and/or mixtures thereof. These initiators may optionally be combined with other radical initiators of the peroxide or azo type and/or with aminic accelerators.

Although cationic polymerization is preferably used, vinyl ethers may also be employed as comonomers. Examples of such vinyl ethers are vinylmethylether, vinylethylether, vinylpropylether, vinylisobutylether, vinyidodecylether, vinyloctadecylether, vinylcyclohexylether, vinyl-4-hydroxybutylether, butanediol-1,4-divinylether, 1,4-cyclohexane dimethanol divinylether, diethyleneglycol divinylether, triethyleneglycol divinylether and the following vinyl compounds: N-vinylpyrrolidone, vinylcaprolactam, 1-vinylimidazole, divinylethylene urea.

The principal components of the compositions according to the invention are used in the following quantities:
a) 1 to 80% by weight, preferably 1 to 40% by weight, of organotitanium, organosilicon and/or organozirconium compound corresponding to formula (I),
b) 20 to 95% by weight, preferably 40 to 90% by weight, of comonomer containing at least 2 double bonds per molecule,
c) 0 to 40% by weight of comonomer containing 1 double bond per molecule,
d) 0.1 to 10% by weight of an initiator or a mixture of initiators,
e) 0 to 30% by weight other additives and auxiliaries.

It is well known to the expert that the components mentioned above, particularly the organometallic compounds, can enter into reactions with one another and, as technical products, can contain impurities so that they are present in the treatment composition in the form which corresponds to the thermodynamic or kinetic equilibrium under the conditions mentioned.

The compositions according to the invention may contain as further additives conductivity pigments or conductive fillers such as, for example, iron phosphide (Ferrophos), vanadium carbide, titanium nitride, carbon black, graphite, molybdenum sulfide or tin- or antimony-doped barium sulfate. Iron phosphide is particularly preferred. The conductivity pigments or fillers are added to improve weldability or to improve coating with electrodeposition paints. These inorganic auxiliaries should be present in fine-particle form, i.e. their mean particle diameters are between 0.005 and 5 μm and preferably between 0.05 and 2.5 μm. The auxiliaries are used in quantities of 0 to 30% by weight.

The compositions may also contain additives for improving forming behavior, for example wax-based derivatives based on natural or synthetic waxes, for example polyethylene, polytetrafluoroethylene (PTFE) or wax derivatives.

Where it is used on metal strip surfaces in particular, the composition is applied in known manner to an optionally metal-coated steel strip or (alloyed) aluminium strip by chemcoating, stripping, by the curtain flow process, by immersion/squeezing or spraying/squeezing at temperatures of 10 to 50° C. and preferably in the range from 15 to 35° C.

The compositions according to the invention are preferably cured or crosslinked by ultraviolet (UV) radiation or by electron beam. Suitable UV radiation has wavelengths of 200 to 800 nm and preferably in the range from 250 to 450 nm. The radiation intensity is determined by the desired application rate, the initiator system and the comonomer composition and may readily be determined by the expert. The electron beam alternatively used may be generated by any conventional electron beam source, for example by an accelerator of the van de Graaff generator, linear accelerator, resonance transformer or dynatron type. The electron beam has an energy of ca. 50 to 1,000 keV and preferably in the range from 100 to ca. 300 keV. The resulting radiation dose is in the range from ca. 0.1 to 100 Mrad.

The formation of the film, the crosslinking of the film and its anchorage on the metal surface are preferably achieved by UV radiation or by electron beam as known per se. The exposure time is between 0.1 and 120 seconds and preferably between 1 and 30 seconds. The coating has a weight per unit area after crosslinking of 0.1 to 10 and preferably 0.5 to 5.0 g/m². The film forming reaction may optionally be supported by the application of heat.

The layers thus produced may be coated with the liquid or powder-form finishing paints typically used in the domestic appliance and/or architectural industries. In addition, the corrosion-inhibiting layer according to the invention may be immediately coated with typical strip finishing paints. The coatings thus produced protect the plate and provide adequate protection against corrosion to DIN 53167 and adequate substrate adhesion to DIN 53151. The corrosion resistance of materials treated with the corrosion-inhibiting composition according to the invention reaches the levels achievable with a conventional coating.

If the treatment according to the invention is carried out immediately after metallic surface finishing, for example electrolytic galvanization or hot-dip galvanization, of steel strip, the strip may be contacted with the treatment solution or dispersion according to the invention without preliminary cleaning. However, if the metal strip to be treated has been stored and/or transported before the treatment according to the invention, it is generally provided with corrosion-inhibiting oils or is at least soiled to such an extent that it has to be cleaned before coating in accordance with the invention. Cleaning may be carried out with conventional mildly to strongly alkaline cleaners or—in the case of aluminium and its alloys—even with acidic cleaners.

The invention is illustrated in the following by a few Examples. As regards the compositions, all quantities are in parts by weight unless otherwise indicated.

The metal plates were cleaned (for 15 secs.) with a 2.5% Ridoline 72 (Henkel) solution heated to 60° C. The plates were then rinsed with deionized water and dried.

The individual components listed in Table 1 were generally processed in the order shown by stirring at room temperature to form a homogeneous mixture.

The UV-curing formulations were then applied by knife coating. The plates thus prepared were then cured by UV radiation until they were tack-free.

A BASF polyester finishing paint was then applied by knife coating and stoved to the manufacturer's specification.

Remarks on the Results Out in the Table:

Commercially available Ti trimethacrylate methoxyethoxy ethoxide was used as the Ti organyl compound; a mixture of 2,4,6-trimethylbenzoyl diphenyl phosphine oxide and 1-hydroxycyclohexyl phenyl ketone was used as the initiator mixture.

Examples 2, 4, 6, 8, 10, 12, 14, 16 correspond to the invention and show a good corrosion-inhibiting effect in the salt spray test to DIN 53167 and good substrate adhesion in the cross hatch adhesion test to DIN 53 151 with and without indentation whereas Comparison Examples 1, 3, 5, 7, 9, 13, 15 show an unsatisfactory corrosion-inhibiting effect and unsatisfactory substrate adhesion. Compositions containing titanium methacrylate triisopropoxide, titanium methacryloxyethyl acetoacetate triisopropoxide, (2-methacryloxyethoxy)-triisopropoxytitanate also produced good results. Favorable curing rates were also achieved by using the following initiators or initiator mixtures of benzil dimethyl ketal, benzophenone, 2-hydroxy-2-methyl-1-phenylpropan-1-one.

| Example | Composition | Coating weight [g/m$^2$] | STT paint creepage DIN 53 167 Hours | Score [mm] one-sided | Edge [mm] | Cross hatch test DIN 53 151 [mm] Indentation Without | With a) 3 mm b) 6 mm |
|---|---|---|---|---|---|---|---|
| 1 | 93.0% Photomer 4017 (Henkel KGaA) 7.0% Initiator (mixture) | 9.5 | 100 | 10.6 | 9.8 | 4 | a) — b) — |
| 2 | 67.9% Photomer 4017 (Henkel KGaA) 27.0% Ti organyl compound 5.1% Initiator (mixture) | 15 | 100 | 0.8 | 1.6 | 0 | a) 1 b) — |
| 3 | 93.0% Ebecryl 408 (ucb Chemicals) 7.0% Initiator (mixture) | 35–40 | 100 | 4.5 | 2.4 | 3 | a) — b) — |
| 4 | 67.9% Ebecryl 408 (ucb Chemicals) 27.0% Ti organyl compound 5.1% Initiator mixture | 10 | 100 | 0.5 | 2.4 | 0 | a) 0 b) 2 |
| 5 | 93.0% Sartomer SR 9051 (Cray Valley) 7.0% Initiator (mixture) | 6 | 100 | 1 | 2.7/1.4 | 0 | a) 0 b) 0 |
| 6 | 67.9% Sartomer SR 9051 (Cray Valley) 27.0% Ti organyl compound 5.1% Initiator (mixture) | 5 | 100 | 1.0 | 2.1 | 0 | a) 0 b) 0 |
| 7 | 93.0% Photomer 8061 (Henkel KGaA) 7.0% Initiator (mixture) | 6 | 100 | Complete flaking | | 2 | a) 5 b) — |
| 8 | 67.9% Photomer 8061 (Henkel KGaA) 27.0% Ti organyl compound 5.1% Initiator (mixture) | 3 | 100 | 3 | 2.4 | 0 | a) 0 b) 0 |
| 9 | 93.0% Photomer 4149 (Henkel KGaA) 7.0% Initiator (mixture) | 7 | 100 | 5 | 3.3 | 0 | a) 5 b) 5 |
| 10 | 67.9% Photomer 4149 (Henkel KGaA) 27.0% Ti organyl compound 5.1% Initiator (mixture) | 5 | 100 | 0.8 | 2.4 | 0 | a) 0 b) 0 |
| 11 | 93.0% Laromer PO 84 F (BASF AG) 7.0% Initiator (mixture) | 4–5 | 100 | 8 | 3 | 5 | a) 5 b) 5 |
| 12 | 67.9% Laromer PO 84 F (BASF AG) 27.0% Ti organyl compound 5.1% Initiator (mixture) | 3 | 100 | 0.8 | 1.5 | 1 | a) 1–2 b) 2 |
| 13 | 93.0% Sartomer C 2000 (Cray Valley) 7.0% Initiator (mixture) | 2–3 | 100 | 0.9 | 1.4 | 1 | a) 2 b) 2 |
| 14 | 67.9% Sartomer C 2000 (Cray Valley) 27.0% Ti organyl compound 5.1% Initiator (mixture) | 2 | 100 | 1.6 | 1.7 | 1 | a) 1 b) 1 |
| 15 | 93.0% Photomer 6230 (Henkel KGaA) 7.0% Initiator (mixture) | 35–63 | | Complete flaking of the PE finishing paint | | — | a) — b) — |
| 16 | 67.9% Photomer 6230 (Henkel KGaA) 27.0% Ti organyl compound 5.1% Initiator (mixture) | 3–7 | 100 | 0.3 | 1.2 | 0 | a) 0 b) 1 |

The invention claimed is:

1. A chromium-free process for inhibiting corrosion of substrates comprising steel, the process comprising the steps of:
   a) contacting a clean, untreated surface comprising steel with a corrosion inhibitor composition for 0.5 to 60 seconds at a treatment temperature of 10° C. to 50° C., said corrosion inhibitor comprising:
      i) one or more compounds of formula (I):

$$(CR^1R^2=CR^3-COO-)_n-Me-(O-X)_{4-n} \quad (I)$$

in which
         $R^1$ and $R^2$ represent H, $C_{1-12}$ alkyl, aralkyl, or the group —CO—O—Y,
         $R^3$ is H or $C_{1-12}$ alkyl,
         Me is a titanium, silicon, or zirconium ion,
         X is H, $C_{1-12}$ alkyl, aryl, aralkyl, alkoxyl, aroxyl, sulfonyl, phosphate, or pyrophosphate,
         Y is H, $C_{1-12}$ alkyl, or Me, and
         n=0 to 4;
      ii) at least one olefinically unsaturated co-monomer containing at least two olefinically unsaturated double bonds per molecule;
      iii) optionally, one or more other co-monomers containing one olefinically unsaturated double bond per molecule; and
      iv) one or more radical or cationic polymerization initiators, or any combination thereof, wherein at least one initiator is activatable by radiation;
   b) removing excess corrosion inhibitor, if any, from the substrate; and
   c) applying a suitable supply of energy for 0.1 to 120 seconds to the corrosion inhibitor to polymerize the monomers and form a polymeric film on the substrate, said polymeric film having a weight per unit area of 0.1 to 10 g/m².

2. The process of claim 1, wherein the treatment temperature in a) is 15° C. to 35° C.

3. The process of claim 1, wherein the at least one olefinically unsaturated co-monomer ii) containing at least two olefinically unsaturated double bonds per molecule comprises one or more esterification products of alkane polyols, polyester polyols, polyether polyols or polyepoxides optionally containing hydroxyl groups with one or more olefinically unsaturated carboxylic acids selected from the group consisting of acrylic acid, methacrylic acid, itaconic acid, crotonic acid, maleic acid, maleic acid semiester, fumaric acid, fumaric acid semiester, reactive carboxyfunctional macromonomers, and mixtures thereof.

4. The process of claim 1, wherein the olefinically unsaturated comonomer ii) comprises one or more esterification products of one or more compounds selected from the group consisting of $C_{2-36}$ diols, polyalkylene glycol diols, $C_{3-12}$ triols, trisalkoxylates of $C_{3-12}$ triols, polyester polyols, polyepoxy compounds, and mixtures thereof with the one or more olefinically unsaturated carboxylic acids.

5. The process of claim 1, wherein the olefinically unsaturated comonomer ii) comprises one or more reaction products of one or more polyurethanes containing free isocyanate groups with one or more OH-functional alkyl (meth)acrylates.

6. The process of claim 1, wherein the corrosion inhibitor comprises 1% to 80% by weight of one or more compounds of formula (I), 20% to 95% by weight of at least one other olefinically unsaturated co-monomer containing at least two olefinically unsaturated double bonds per molecule, 0% to 40% by weight of the one or more other co-monomers containing one olefinically unsaturated double bond per molecule, 0.1% to 10% by weight of the one or more initiators, and 0% to 30% by weight of other additives and auxiliaries.

7. The process of claim 1, wherein the corrosion inhibitor comprises 1% to 40% by weight of one or more compounds of formula (I) and 40% to 90% by weight of at least one other olefinically unsaturated co-monomer containing at least two olefinically unsaturated double bonds per molecule.

8. A chromium-free process for inhibiting corrosion of substrates comprising steel, the process comprising the steps of:
   a) applying a corrosion inhibitor composition directly to a clean, unphosphated steel surface for 0.5 to 60 seconds at a treatment temperature of 10° C. to 50° C., said corrosion inhibitor comprising:
      i) one or more compounds of formula (I):

$$(CR^1R^2=CR^3-COO-)_n-Me-(O-X)_{4-n} \quad (I)$$

in which
         $R^1$ and $R^2$ represent H, $C_{1-12}$ alkyl, aralkyl, or the group —CO—O—Y,
         $R^3$ is H or $C_{1-12}$ alkyl,
         Me is a titanium, silicon, or zirconium ion,
         X is H, $C_{1-12}$ alkyl, aryl, aralkyl, alkoxyl, aroxyl, sulfonyl, phosphate, or pyrophosphate,
         Y is H, $C_{1-12}$ alkyl, or Me, and
         n=0 to 4;
      ii) at least one olefinically unsaturated co-monomer containing at least two olefinically unsaturated double bonds per molecule;
      iii) optionally, one or more other co-monomers containing one olefinically unsaturated double bond per molecule; and
      iv) one or more radical or cationic polymerization initiators, or any combination thereof, wherein at least one initiator is activatable by radiation;
   b) removing excess corrosion inhibitor, if any, from the unphosphated steel surface; and
   c) applying a suitable supply of energy for 0.1 to 120 seconds to the corrosion inhibitor to polymerize the monomers and form a corrosion inhibiting film on the unphosphated steel surface, said corrosion inhibiting film having a weight per unit area of 0.1 to 10 g/m².

9. The chromium-free process of claim 8 wherein Me is titanium.

10. A chromium-free process for inhibiting corrosion of substrates comprising steel, the process comprising the steps of:
   a) applying a corrosion inhibitor composition directly to a clean, unphosphated metal surface, said surface being aluminum, alloys of aluminum or steel, said steel optionally provided with a metallic coating of zinc, aluminum, copper or nickel, or any combination thereof, for 0.5 to 60 seconds at a treatment temperature of 10° C. to 50° C., said corrosion inhibitor comprising:
      i) one or more compounds of formula (I):

$$(CR^1R^2=CR^3-COO-)_n-Me-(O-X)_{4-n} \quad (I)$$

in which
         $R^1$ and $R^2$ represent H, $C_{1-12}$ alkyl, aralkyl, or the group —CO—O—Y,
         $R^3$ is H or $C_{1-12}$ alkyl,
         Me is a titanium, silicon, or zirconium ion,
         X is H, $C_{1-12}$ alkyl, aryl, aralkyl, alkoxyl, aroxyl, sulfonyl, phosphate, or pyrophosphate, Y is H, $C_{1-12}$ alkyl, or Me, and
n=0 to 4;
ii) at least one olefinically unsaturated co-monomer containing at least two olefinically unsaturated double bonds per molecule;
iii) optionally, one or more other comonomers containing one olefinically unsaturated double bond per molecule; and
iv) one or more radical or cationic polymerization initiators, or any combination thereof, wherein at least one initiator is activatable by radiation;

b) removing excess corrosion inhibitor, if any, from the unphosphated steel surface; and
c) applying a suitable supply of energy for 0.1 to 120 seconds to the corrosion inhibitor to polymerize the monomers and form a corrosion inhibiting film on the unphosphated steel surface, said corrosion inhibiting film having a weight per unit area of 0.1 to 10 $g/m^2$.

* * * * *